(12) United States Patent
Gottsche et al.

(10) Patent No.: US 9,283,380 B2
(45) Date of Patent: Mar. 15, 2016

(54) EXTERNAL PACEMAKER WITH AN ELECTRODE TEMPORARILY CONNECTABLE TO A HEART AND COUPLED VIA A PLUG CONNECTOR

(71) Applicant: Osypka AG, Rheinfelden-Baden (DE)

(72) Inventors: Thorsten Gottsche, Rheinfelden (DE); Astrid Virnich, Rheinfelden (DE); Maik Grafe, Rheinfelden (DE)

(73) Assignee: OSYPKA AG, Rheinfelden-Baden (DE)

( * ) Notice: Subject to any disclaimer, the term of this patent is extended or adjusted under 35 U.S.C. 154(b) by 0 days.

(21) Appl. No.: 14/160,949

(22) Filed: Jan. 22, 2014

(65) Prior Publication Data

US 2014/0207223 A1    Jul. 24, 2014

(30) Foreign Application Priority Data

Jan. 22, 2013   (DE) .......................... 10 2013 001021

(51) Int. Cl.

| | | |
|---|---|---|
| *A61N 1/00* | (2006.01) | |
| *A61N 1/05* | (2006.01) | |
| *A61N 1/375* | (2006.01) | |
| *A61N 1/39* | (2006.01) | |
| *A61N 1/362* | (2006.01) | |

(52) U.S. Cl.
CPC .............. *A61N 1/056* (2013.01); *A61N 1/0563* (2013.01); *A61N 1/3625* (2013.01); *A61N 1/375* (2013.01); *A61N 1/3968* (2013.01)

(58) Field of Classification Search
CPC ... A61N 1/056; A61N 1/0563; A61N 1/3625; A61N 1/375; A61N 1/3968
See application file for complete search history.

(56) References Cited

U.S. PATENT DOCUMENTS

| | | |
|---|---|---|
| 5,000,177 A | 3/1991 | Hoffmann et al. |
| 5,275,620 A | 1/1994 | Darby et al. |
| 5,557,210 A | 9/1996 | Cappa et al. |
| 2003/0077935 A1 | 4/2003 | Stein et al. |
| 2007/0099487 A1 | 5/2007 | Osypka |
| 2011/0071584 A1* | 3/2011 | Mokelke et al. .................. 607/4 |
| 2011/0160824 A1 | 6/2011 | Ware et al. |

* cited by examiner

*Primary Examiner* — George Manuel
(74) *Attorney, Agent, or Firm* — Volpe and Koenig, P.C.

(57) ABSTRACT

An external pacemaker with at least one electrode temporarily connectable to the heart, and at the distal end of which is an active region, which makes contact with heart tissue, and at the proximal end is a contact plug. The electrode is for transmission of stimulation, defibrillation, and/or cardioversion pulses and is plugged into a pacemaker plug socket. The contact plug has first and second contact regions at its plug part. The plug socket matches the contact plug with two mating contacts, the first for transmitting stimulation pulses and the second for transmitting defibrillation and/or cardioversion pulses. In the plugged-in position, only the contact region on the plug part makes contact with the mating contact provided for transmitting the defibrillation and/or cardioversion pulses, such that no defibrillation and/or cardioversion pulse can be transmitted to electrodes which are unsuitable for defibrillation and/or cardioversion and have only a single-stage contact plug.

19 Claims, 10 Drawing Sheets

EXTERNAL PACEMAKER WITH AN ELECTRODE TEMPORARILY CONNECTABLE TO A HEART AND COUPLED VIA A PLUG CONNECTOR

INCORPORATION BY REFERENCE

The following documents are incorporated herein by reference as if fully set forth: German Patent Application No. 102013001021.7, filed Jan. 22, 2013.

FIELD OF THE INVENTION

The invention relates to an external pacemaker comprising at least one electrode which can be temporarily connected to the heart and at the distal end of which is arranged at least one active region which makes contact with tissue of the heart of a patient in the position of use, wherein the electrode, in the position of use, is joinable or joined to the external pacemaker by the proximal end of said electrode via at least one plug connector, formed of two parts, namely of a contact plug and a plug socket, for transmitting stimulation pulses from the external pacemaker to the heart of the patient, and wherein the electrode, at least at its active region which makes contact with the tissue of the heart, has a surface area large enough for the transmission or emission of a defibrillation and/or cardioversion pulse.

BACKGROUND

Such an external pacemaker is used to support the cardiac function particularly after operative interventions on the human heart. In this case, it can function as a pure pacemaker and emit stimulation pulses to the heart in order to predetermine a specific pulse frequency or a specific cardiac rhythm and/or to avoid possibly dangerous cardiac arrhythmias.

In acute emergencies, for example if the patient suffers a dangerous cardiac arrhythmia, in particular ventricular fibrillation, it may be necessary also to emit a defibrillation and/or cardioversion pulse to the heart in order to eliminate the cardiac arrhythmia.

However, if an electrode suitable only for the pacemaker stimulation is used in such an emergency, an additional defibrillation and/or cardioversion device is required for the defibrillation and/or cardioversion.

SUMMARY

Therefore, it is an object of the invention to provide an external pacemaker which, on the one hand, is suitable both for stimulation and for defibrillation and/or cardioversion, but in the case of which, on the other hand, the emission of defibrillation and/or cardioversion pulses to an electrode which is unsuitable for defibrillation and/or cardioversion is prevented.

In order to achieve this object, in the case of an external pacemaker defined in the introduction it is provided that the contact plug of the plug connector has a first and a second electrical contact region and the plug socket of the plug connector, in a manner matching that, has a first and a second electrical mating contact, wherein the two contact regions or the two mating contacts of that part of the plug connector which is arranged at the external pacemaker are wire-able or wired differently, such that one of the two contact regions or mating contacts is designed for transmitting stimulation pulses and the other of the two contact regions or mating contacts is designed for transmitting defibrillation and/or cardioversion pulses to the electrode, and wherein the external pacemaker is connected to a defibrillator and/or cardioverter and/or contains a defibrillator and/or a cardioverter and/or is designed for emitting defibrillation and/or cardioversion pulses. It is thus possible to use the external pacemaker both for stimulation and for—possibly necessary in acute cases—defibrillation and/or cardioversion of the heart.

It is possible for the plug socket of the at least one plug connector to be provided at the proximal end of the electrode and for the contact plug to be provided on the external pacemaker.

In one preferred embodiment of the invention, however, the contact plug of the at least one plug connector is arranged at the proximal end of the electrode and the plug socket of the plug connector is arranged at the external pacemaker.

In this case, the two electrical mating contacts of the plug socket can be wire-able or wired differently in such a way that one of the two mating contacts is designed for transmitting stimulation pulses and the other of the two mating contacts is designed for transmitting defibrillation and/or cardioversion pulses respectively via the corresponding contact region of the contact plug to the electrode.

For transmitting defibrillation and/or cardioversion pulses, only electrodes which are also suitable for cardioversion and/or defibrillation have at least one contact plug according to the invention having two contact regions, with the result that the defibrillation and/or cardioversion pulses can be emitted by the pacemaker only to an electrode having such a contact plug.

Conventional electrodes suitable only for stimulation, due to their customary contact plug, cannot make contact with the mating contact for the transmission of defibrillation and/or cardioversion pulses of the plug socket, with the result that transmission of defibrillation and/or cardioversion pulses to an electrode provided with a customary contact plug can be avoided. As a result, the risk of injury to the heart on account of defibrillation and/or cardioversion pulse emission via an electrode unsuitable for this can be reduced or even ruled out.

The incorrect wiring of an electrode which is unsuitable on account of the form of its contact plug can be avoided particularly effectively if the two differently wire-able or wired mating contacts of the plug socket are shaped differently and the two contact regions of the contact plug are shaped in a manner matching the mating contacts, and/or if the two contact regions of the contact plug are embodied as two plug parts matching the two mating contacts of the plug socket. The plug socket, at least in its interior, can therefore be configured in two stages, for example, and the contact plug can be configured in a manner matching that or complementarily with respect thereto.

In this way, it is possible that only a correspondingly shaped contact plug can be plugged into the plug socket such that its two contact regions make contact with the two mating contacts of the plug socket, in order to be able to transmit, besides stimulation pulses, if necessary, also defibrillation and/or cardioversion pulses to an electrode coupled to the contact plug.

With customary contact plugs, which do not have the two contact regions shaped in a manner matching the two mating contacts of the plug socket and/or do not have the two plug parts provided as contact regions, it is possible to prevent contact from being made inadvertently with the mating contact for the emission of defibrillation and/or cardioversion pulses.

It is thus possible to equip electrodes which are provided and/or suitable exclusively for stimulation, but not for defibrillation and/or cardioversion, with customary contact plugs which, although they make contact with the mating contact of the plug socket for the emission of stimulation pulses, do not reach the mating contact of the plug socket for the emission of defibrillation and/or cardioversion pulses even in the plugged-in position of use.

Inadvertent transmission of a defibrillation and/or cardioversion pulse to such electrodes can thus be effectively avoided.

For the different configuration of the mating contacts of the plug socket, the first and second mating contacts of the plug socket can be arranged one behind the other in the plug-in direction of the contact plug and have two internal cross sections of different sizes, as a result of which a contact plug with which no defibrillation and/or cardioversion pulses are permitted to be transferred and which has only one contact region matching the first mating contact cannot be plugged incorrectly.

For this purpose, it may be expedient if the first mating contact of the plug socket has a larger internal cross section than the second mating contact and is embodied as a contact area for transmitting stimulation pulses to the electrode, and if the second mating contact of the plug socket, said second mating contact being adjacent in the plug-in direction of the contact plug, has a smaller internal cross section than the first mating contact and is embodied as a contact area for transmitting defibrillation and/or cardioversion pulses to the electrode.

In this case, it is also conceivable, of course, for the first mating contact of the plug socket in the plug-in direction of the contact plug to be designed as a contact area for transmitting defibrillation and/or cardioversion pulses, and for the second mating contact in the plug-in direction of the contact plug to be designed as a contact area for transmitting stimulation pulses to the electrode.

In both cases, however, the first and second mating contacts in the interior of the plug socket are electrically isolated or insulated from one another in such a way that only the mating contact provided for stimulation can transmit the stimulation pulse and only the mating contact provided for defibrillation and/or cardioversion can transmit the defibrillation and/or cardioversion pulse, that is to say that it is not possible for the pulses to jump over to the respective other mating contact.

In this case, the first mating contact having the larger internal cross section, in the position of use, can be arranged in a manner adjoining an entrance opening of the plug socket for the contact plug, and the second mating contact having the smaller internal cross section can follow therebehind in the plug-in direction of the contact plug, that is to say can lie deeper in the interior of the plug socket.

In order to secure the contact plug that has been plugged into the plug socket in the position of use and in order to protect it against unintentional withdrawal, the plug socket can have in the first mating contact a collet form and/or a slotted region having individual fingers which can be compressed by a union nut and a conical region, and/or can have contact springs in the second mating contact.

However, it is also possible for a cross-sectionally thinner first part of the contact plug, said first part fitting into the second mating contact of the plug socket, to be slotted and/or elastically deformable, and for the contact plug, in the position of use, to be held and/or fixedly clamped in a force-locking manner in the plug socket by at least one of the contact regions of said contact plug.

In order to secure the contact plug in its plugged-in position of use in the plug socket, it is also possible to fix the contact plug to the plug socket by a screw and/or a screw connection.

In this case, the screw can act on a grip piece of the contact plug and/or on one or on both contact regions of the contact plug.

In order to enable the contact plug to be seated well in its plugged-in position of use and to enable a good electrical connectivity, the plug parts forming the two contact regions of the contact plug and matching the two mating contacts of the plug socket can be arranged one behind the other in the plug-in direction of the contact plug and can be embodied with different cross sections such that the second plug part of the contact plug, which makes contact with the first mating contact of the plug socket in the plugged-in position of use, at least in regions projects radially beyond the first plug part of the contact plug, which first plug part is arranged behind said second plug part in the axial direction and makes contact with the second mating contact of the plug socket in the plugged-in position of use. In this regard, the contact plug for the electrode suitable for defibrillation and/or cardioversion can likewise have a two-stage form matching the plug socket.

By way of example, the first and second plug parts of the contact plug each can have a closed and/or circular cross section, or at least one of the two plug parts of the contact plug can have a cross section which deviates from a circular form and which is, in particular, oval or triangular or quadrilateral or polygonal or circular with at least one flattened portion. The plug socket can consequently function as a lock and the contact plug as a key in order to ensure that the contact region of the contact plug which is provided for transmitting stimulation pulses does not come into contact with that mating contact of the plug socket which is designed for emitting defibrillation and/or cardioversion pulses.

However, the contact plug can also be configured in such a way that one of the two plug parts of the contact plug has a polygonal, in particular triangular, cross section, that is to say has the form of a prism, and the other plug part of the contact plug has a round cross section, that is to say is cylindrical. In the case also of this configuration of the contact plug and a corresponding configuration of the plug socket, incorrect wiring of the electrode can be avoided.

Alternatively, the second plug part of the contact plug having the larger cross section can have a circular cross section, while the first plug part of the contact plug having the smaller cross section has an arbitrary cross-sectional shape, wherein the largest dimension of the first, smaller plug part is enclosed by the projection of the circular cross section of the second, larger plug part of the contact plug. In this way, too, assuming a plug socket configured in a manner matching the contact plug, incorrect contact-making of the contact plug can be avoided.

In order to make it easier for the contact plug to be plugged into the plug socket, the longitudinal central axes of the two plug parts of the contact plug can be arranged coaxially with respect to one another and/or in alignment with one another. In the case of longitudinal central axes of the two plug parts of the contact plug that are in alignment with one another, the plug does not have to be oriented for plugging into the correspondingly configured plug socket, but rather can center itself during plugging into the plug socket and can thus be guided into its plugged-in position of use in a particularly simple manner.

This can be advantageous particularly when the contact plug, for example in an emergency situation, has to be plugged into the plug socket at the external pacemaker particularly rapidly and particularly securely.

However, it is also conceivable for the longitudinal central axes of the two plug parts of the contact plug to be arranged parallel, in particular in a manner running offset with respect to one another.

The electrode can be designed for bipolar and/or quadripolar and/or multipolar stimulation and/or defibrillation and/or for cardioversion by virtue of the fact that it has at least two or four or more poles, and by virtue of the fact that a respective plug connector, consisting of a contact plug and a plug socket, is provided for each pole of the electrode.

The electrode can therefore have a respective contact plug for each pole at its proximal end and the pacemaker can have at least one plug socket for each contact plug, wherein at least one of the two plug sockets is equipped with the two differently wire-able and differently configured mating contacts and at least the contact plug plugged in said plug socket in the position of use is equipped with the two plug parts matching the two mating contacts of the plug socket as contact regions.

The use of a bipolar or quadripolar electrode instead of a monopolar electrode may be preferable since, in the case of a bipolar electrode or else a quadripolar electrode, a further electrode that can be fitted in or on the patient in another way can be dispensed with.

Particularly in the case of electrodes having two or more poles, it may be expedient for good transfer of the stimulation and/or defibrillation and/or cardioversion pulses to the heart if the electrode has at its distal end at least one second active region which makes contact with the tissue of the heart of a patient, and/or if at least one pole, in particular two poles, is/are arranged at each active region.

The contact plug can be already connected to the electrode in the delivery state thereof and/or be subsequently connectable to the electrode and/or couplable thereto. If the contact plug is subsequently connectable to the electrode and/or couplable thereto, it is possible to use the contact plug according to the invention with different electrodes, including electrodes suitable for defibrillation and/or cardioversion, and/or to exchange them as necessary.

The electrode can be embodied as a cardiac wire, which, after a cardiosurgical intervention, for example, can be fixable externally to the heart, in particular sewn to the tissue of the heart and/or anchored therein. This type of electrodes is often used after cardiosurgical interventions and used for postoperative, temporary stimulation of the heart in combination with an external pacemaker.

However, the electrode can also be embodied as an intracardially feedable catheter, in particular with a contact plug arranged at the proximal end, said catheter preferably being advanced from outside via a blood vessel into the interior of the heart, in order there to stimulate, defibrillate and/or cardiovert the heart.

BRIEF DESCRIPTION OF THE DRAWINGS

A number of exemplary embodiments of the invention are described in greater detail below with reference to the drawing. In the Figures, in partly schematic illustration.

DETAILED DESCRIPTION OF THE PREFERRED EMBODIMENTS

An external pacemaker, designated in its entirety by 1, comprises at least one electrode 2, 2a, 2b, 2c, 2d which can be temporarily connected to a heart 5.

At least one active region 6 which makes contact with tissue 4 of the heart 5 of a patient in the position of use of the electrode 2, 2a, 2b, 2c, 2d is situated at a distal end 3 of the electrode 2, 2a, 2b, 2c, 2d, via which at least one active region electrical pulses can be emitted from the pacemaker 1 to the heart 5.

The active region 6 is positioned in the tissue 4 of the heart 5 with the aid of a cardiac needle 6a, with the result that said active region makes contact directly with the tissue 4 of the heart 5.

In another configuration of the invention (cf. FIG. 14), the active region 6 makes contact with tissue or the tissue 4 of the heart 6 indirectly, for example via an electrically conductive body fluid, such that direct contact with the tissue 4 is not necessary for transmitting electrical pulses to the heart 5.

The electrode 2, 2a, 2b, 2c, 2d is connected to the external pacemaker 1 via at least one plug connector, including a contact plug 8 and a plug socket 9. For this purpose, the electrodes 2, 2a, 2b, 2c, 2d illustrated in the Figures have, at their proximal ends 7 facing the pacemaker 1 in the position of use, in each case at least one contact plug 8 and 8a which, for the purpose of coupling the respective electrodes 2, 2a, 2b, 2c and 2d to the external pacemaker 1 and for the purpose of transmitting stimulation pulses from the external pacemaker 1 to the patient's heart 5, can be plugged into the at least one plug socket 9 arranged at the external pacemaker 1 and is plugged in in the position of use.

In another embodiment (not illustrated) of the invention, the at least one contact plug 8 and/or 8a can be arranged at the external pacemaker 1 and the at least one plug socket 9 can be arranged at the proximal end 7 of the electrode 2, 2a, 2b, 2c and 2d.

In order to facilitate the handling of the contact plugs 8 and 8a, in particular during plugging in and unplugging, all of the contact plugs 8, 8a illustrated in the Figures each have a grip 80.

Figure 6:
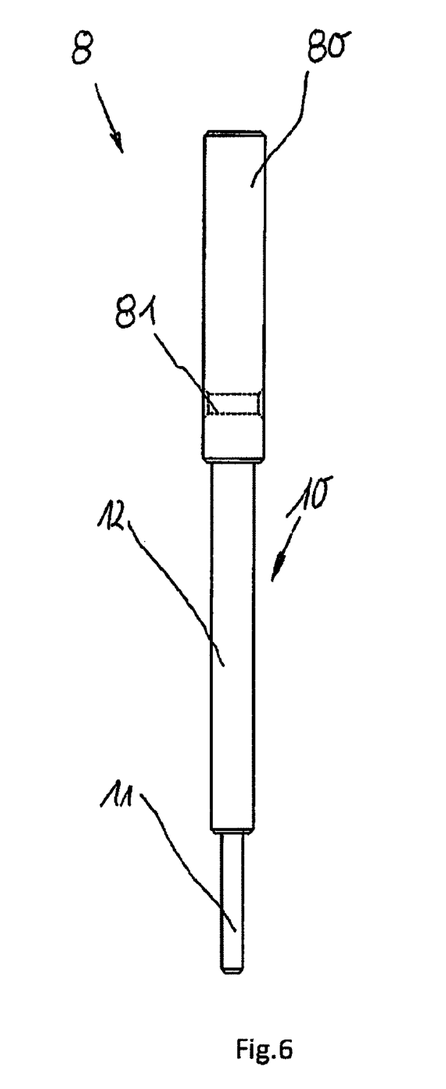
FIG. 6 shows an illustration of a two-stage contact plug according to the invention having two contact regions, wherein the contact plug has a transverse hole for the coupling and the fixing of an electrode.
Figure 7:
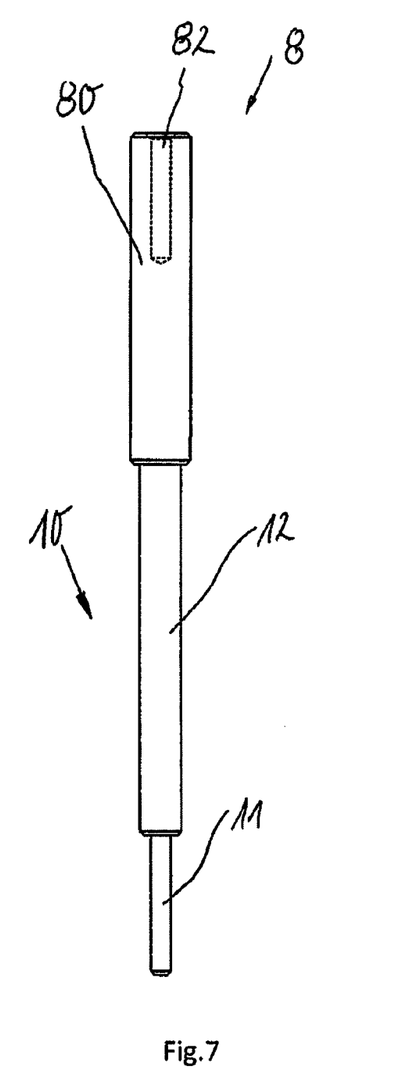
FIG. 7 shows an illustration similar to FIG. 6 of a further two-stage contact plug according to the invention having two contact regions, wherein the contact plug has a longitudinal hole for the coupling of an electrode.

FIGS. 6 and 7 show possible embodiments of the contact plug 8. For electrodes 2, 2a, 2b, 2c, 2d which still do not have a two-stage contact plug 8, these contact plugs 8 can also be used as adapters and subsequently be connected to the electrode 2, 2a, 2b, 2c, 2d and/or coupled thereto.

In accordance with FIG. 6, the contact plug 8 has a transverse hole 81 for the purpose of coupling an electrode 2, 2a, 2b, 2c, 2d, which transverse hole penetrates through the grip 80 of the contact plug 8 and a conductor end of the electrode 2, 2a, 2b, 2c, 2d, insulation having been stripped from said conductor end, can be positioned and fixed in said transverse hole.

In accordance with FIG. 7, the contact plug 8 has a longitudinal hole 82 in its grip 80, said longitudinal hole serving for receiving and coupling an electrode 2, 2a, 2b, 2c, 2d to the contact plug 8.

The fixing mechanisms by which the electrode 2, 2a, 2b, 2c, 2d is held at the respective contact plug 8 are not illustrated, but can be formed for example by a tube segment.

Each of the electrodes 2, 2a, 2b, 2c, 2d illustrated has at least one active region 6 which acts on the heart 5 in the position of use and which has a surface area large enough for the transmission or emission of a defibrillation and/or cardioversion pulse and via which the stimulation and/or defibrillation and/or cardioversion pulses are transmitted to the heart 5.

For positioning the active region 6 in the tissue of the heart 5, the electrodes 2, 2a, 2b and 2c each have at least one cardiac needle 6a which can be separated, in particular cut off or broken off, from the electrode 2, 2a, 2b, 2c, after the positioning of the active region 6.

For the transmission of stimulation pulses and defibrillation and/or cardioversion pulses to the electrode 2, 2a, 2b, 2c, 2d, the contact plug 8 in the position of use has a contact 10 having a first and having a second contact region 11 and 12 and the plug socket 9 arranged at the external pacemaker 1 has, in a manner matching that, two differently wire-able mating contacts 13 and 14.

In this case, the mating contact 13 is designed for transmitting stimulation pulses and the mating contact 14 is designed for transmitting defibrillation and/or cardioversion pulses via the contact plug 8 to the electrode 2, 2a, 2b, 2c, 2d.

The mating contact 13 is supplied by a power source 13a and the mating contact 14 is supplied by a power source 14a.

The external pacemaker 1 is designed for defibrillation and/or cardioversion and/or has, for the purpose of providing defibrillation pulses and/or cardioversion pulses, a defibrillator and/or cardioverter (not illustrated in the Figures) or is connected to such a defibrillator and/or cardioverter.

As shown in FIGS. 1 to 5 and FIGS. 7 and 8, the two differently wire-able or wired mating contacts 13 and 14 of the plug socket 9 are shaped differently. For this purpose, the first and second mating contacts 13 and 14 of the plug socket 9 are arranged one behind the other in the plug-in direction of the contact plug 8 and have internal cross sections of different sizes.

Figure 8:
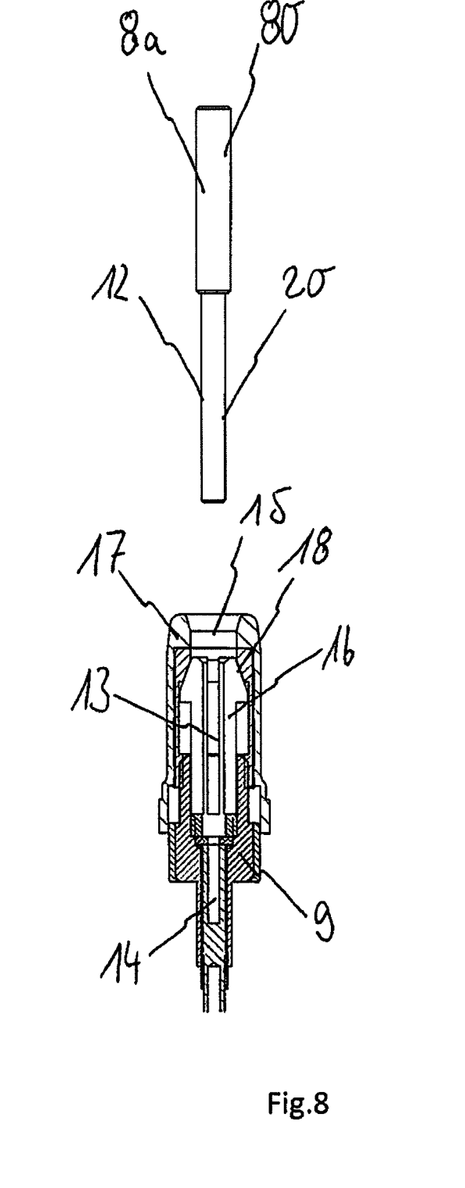
FIG. 8 shows—illustrated in longitudinal cross-section—a plug socket according to the invention with a two-stage contact plug according to the invention, said contact plug not having been plugged in, wherein two mating contacts arranged one behind the other in the plug-in direction of the contact plug can be discerned in the interior of the plug socket.

As shown in particular in FIGS. 7 and 8, in this case the first mating contact 13 of the plug socket 9 has a larger internal cross section than the second mating contact 14, which moreover is also arranged even deeper in the interior of the plug socket 9.

The first mating contact 13, as already explained, is designed as a contact area for transmitting stimulation pulses to the electrode 2, 2a, 2b, 2c, 2d, while the second mating contact 14 of the plug socket 9, said second mating contact being adjacent in the plug-in direction of the contact plug 8, is designed as a contact area for transmitting defibrillation and/or cardioversion pulses to the electrode 2, 2a, 2b, 2c, 2d.

In an embodiment which is not illustrated, however, it is also possible for the second mating contact 14 of the plug socket 9 to be designed for transmitting stimulation pulses and for the first mating contact 13 of the plug socket 9 to be designed for transmitting defibrillation and/or cardioversion pulses to the electrode 2, 2a, 2b, 2c, 2d and thus to the heart 5.

In this case, the first mating contact 13 having the larger internal cross section, in the position of use, adjoins an entrance opening 15 of the plug socket 9 for the contact plug 8, while the second mating contact 14 having the smaller internal cross section is adjacent therebehind in the plug-in direction of the contact plug 8. The second mating contact 14 is therefore arranged deeper in the interior of the plug socket 9 than the first mating contact 13.

In order to be able to fix the contact plug 8 in its position of use and to avoid unintentional withdrawal of the contact plug from its position of use, the plug socket has a collet 16 in the first mating contact 13, which collet can be compressed by a union nut 17 and/or a union part having an internal thread and a conical region 18 acted on by the union nut 17 during tightening, with the result that the contact plug 8 is fixable in its position of use in the plug socket 9.

In an embodiment which is not illustrated, however, the plug socket 9 can also have contact springs in the second mating contact 14 and/or a cross-sectionally thinner first part of the contact plug 8, said first part fitting into the second mating contact 14 of the plug socket 9, can be slotted and/or elastically deformable, with the result that in this configuration of the plug socket 9 as well the contact plug 8, in the position of use, is held and/or fixedly clamped in a force-locking manner in the plug socket 9 by at least one of the contact regions 11, 12 of said contact plug.

The two contact regions 11 and 12 of the contact plug 8 are embodied as two plug parts 19 and 20 matching the two mating contacts 13 and 14 of the plug socket 9 and arranged one behind the other in the plug-in direction and have different cross sections or diameters, such that the second plug part 20 of the contact plug 8, which makes contact with the first mating contact 13 of the plug socket 9 in the plugged-in position of use, at least in regions projects radially beyond the first plug part 19 of the contact plug 8, which first plug part is arranged behind said second plug part in the axial direction and makes contact with the second mating contact 14 of the plug socket 9 in the plugged-in position of use.

In the present exemplary embodiment, the first and second plug parts 19 and 20 each have a circular cross section. However, it is also possible for at least one of the two plug parts 19 or 20 to have a cross section which deviates from a circular form and which is, in particular, oval or triangular or quadrilateral or polygonal or circular with at least one flattened portion.

In another embodiment (likewise not illustrated) of the contact plug 8, one of the two plug parts 19 or 20 can have a polygonal, in particular triangular, cross section, that is to say can have the form of a prism, and the other plug part 19 or 20 can have a round cross section, that is to say can be cylindrical.

In order to effectively avoid the incorrect contact-making and/or the incorrect allocation of the electrode 2, 2a, 2b, 2c, 2d, in a further embodiment (not illustrated) of the contact plug 8 it is provided that the second plug part 20 having the larger cross section has a circular cross section, while the first plug part 19 having the smaller cross section has an arbitrary cross-sectional shape, wherein the largest dimension of the first, smaller plug part 19 is enclosed by the projection of the circular cross section of the second, larger plug part 20.

The longitudinal central axes of the two plug parts 19 and 20 of the contact plug 8 are arranged coaxially with respect to one another and in alignment with one another. This facilitates insertion of the contact plug 8 into the plug socket 9 since the contact plug 8, on account of the coaxial nature of its two plug parts 19 and 20 and the plug socket 9 embodied in a manner matching that with its mating contacts 13 and 14, centers itself during insertion, that is to say does not first have to be manually rotated into an orientation that is correct for insertion.

Figure 9:
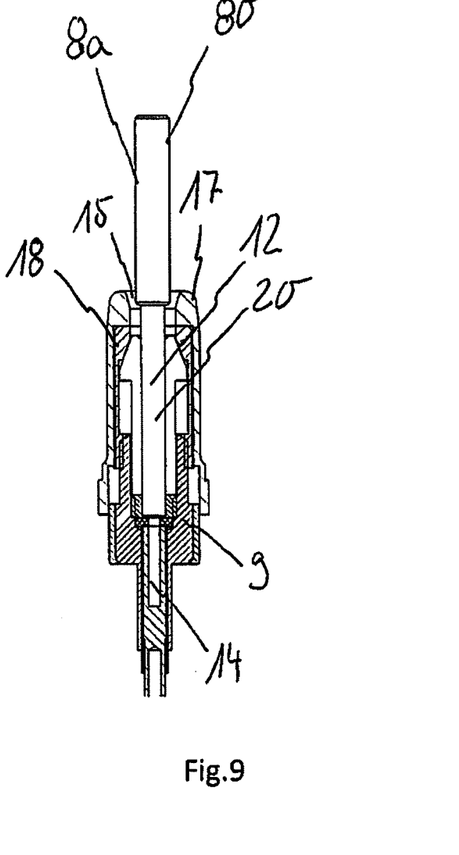
FIG. 9 shows the plug socket illustrated in FIG. 7 with the contact plug likewise illustrated in FIG. 7 in the plugged-in position of use, wherein one mating contact of the plug socket makes contact with one of the two contact regions of the contact plug and the other mating contact makes contact with the other contact region of the contact plug.
Figure 10:
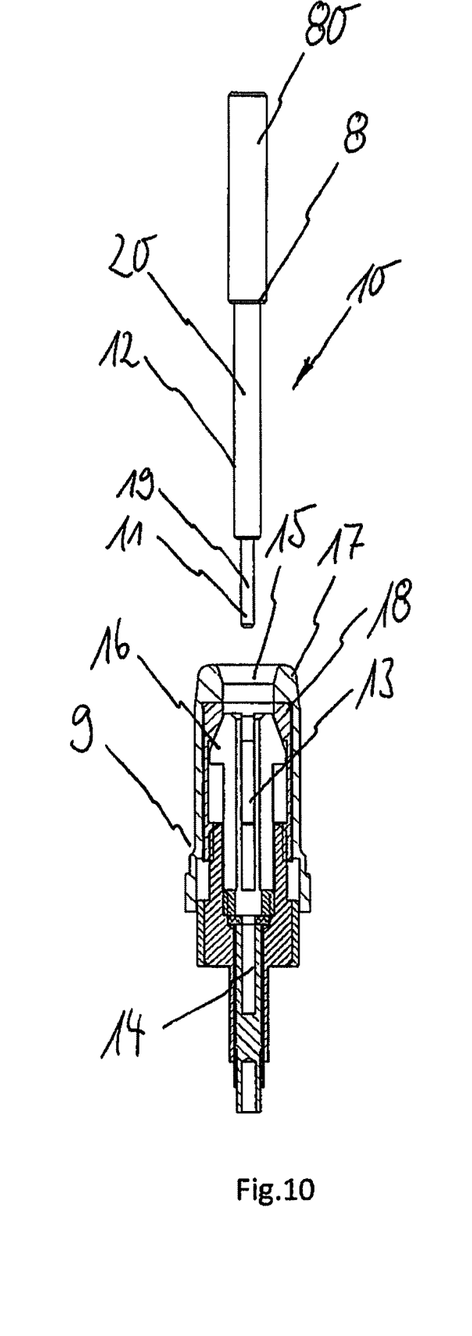
FIG. 10 shows the plug socket illustrated in FIGS. 8 and 9 with a conventional, single-stage contact plug.

FIGS. 8 and 9 illustrate the use of a conventional contact plug 8a with the plug socket 9 according to the invention. A conventional contact plug 8a is preferably used when the function of defibrillation and/or cardioversion of the pacemaker 1 is not intended to be used or is not required. Such contact plugs 8a are usually combined with electrodes which are used only for stimulation, that is to say, for purely pacemaker activity.

As is evident with reference to the Figures, although the conventional contact plug 8a is insertable into the plug socket 9, on no account does it pass, with the contact region 12 formed at its sole plug part 20, only into the region of the mating contact 13 and not into the region of the mating contact 14 of the plug socket 9, which is correspondingly wired for transmitting defibrillation and/or cardioversion pulses to an electrode suitable for this purpose.

The use of conventional electrodes having conventional contact plugs 8a with the pacemaker 1 is therefore possible, but emission of defibrillation and/or cardioversion pulses, which is to be avoided and which might lead to injury to the heart 5 owing to the lack of suitability of the conventional electrode provided only for stimulation, is ruled out.

Figure 1:
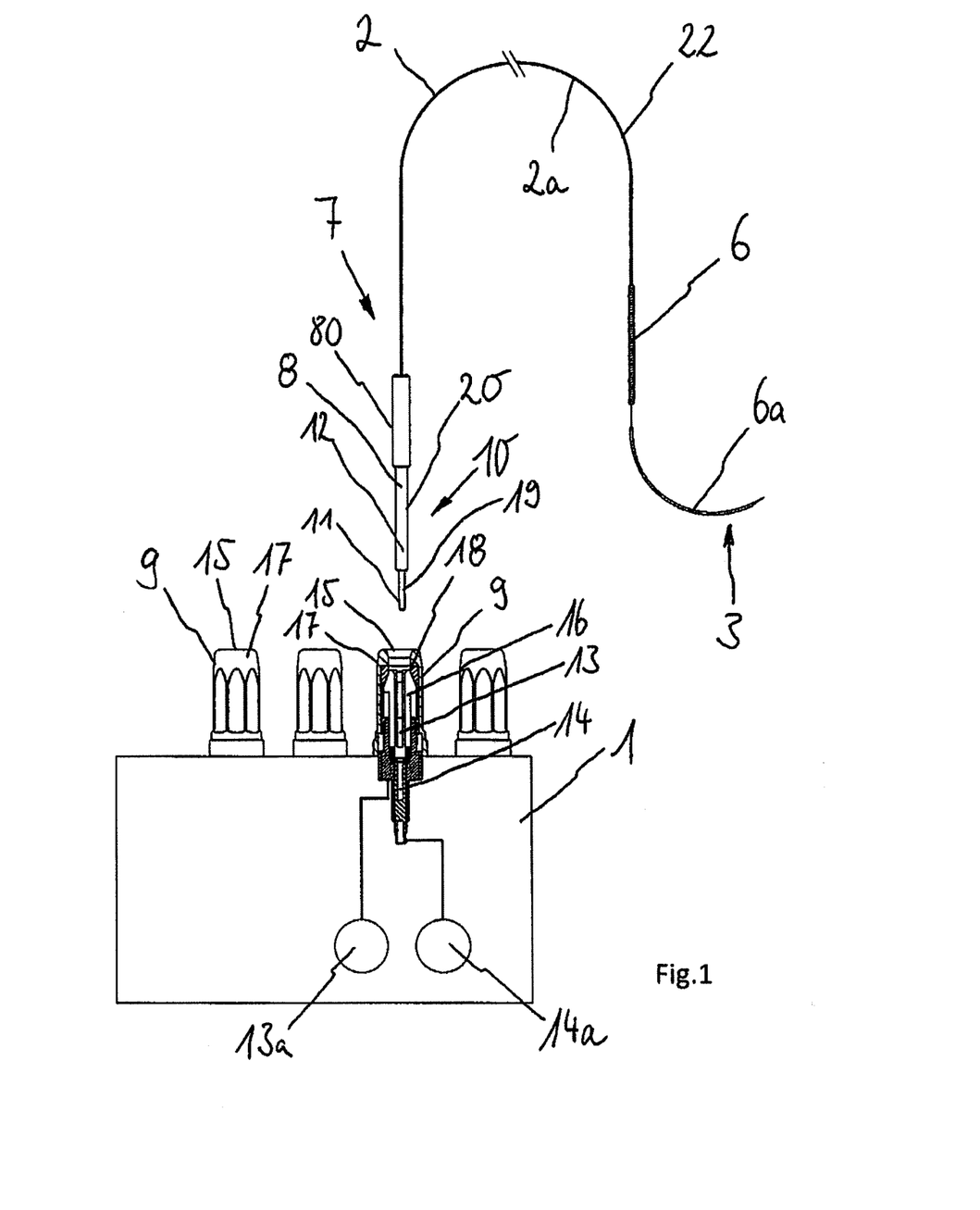
FIG. 1 shows a schematic illustration of an external pacemaker comprising four plug sockets, one of which is illustrated in section, and comprising a unipolar electrode having an active region, which makes contact with tissue of the heart, at its distal end and a contact plug at its proximal end, facing the external pacemaker, wherein the contact plug is embodied as a multi-stage plug having two different contact regions.

The electrode connected to the external pacemaker 1 in accordance with FIG. 1 is a unipolar electrode 2a suitable for unipolar and/or monopolar stimulation and/or defibrillation and/or cardioversion.

For carrying out stimulation, defibrillation and cardioversion, in this case a second electrode should be used, which should be fitted elsewhere on or in the body, in particular on the spine, of a patient and forms a second pole or opposite pole.

It is thus possible to conduct the current required for the stimulation and defibrillation and for the cardioversion away from the electrode 2a to the patient's heart 5 and finally via the second, externally applied electrode (not illustrated in the Figures).

Figure 2:
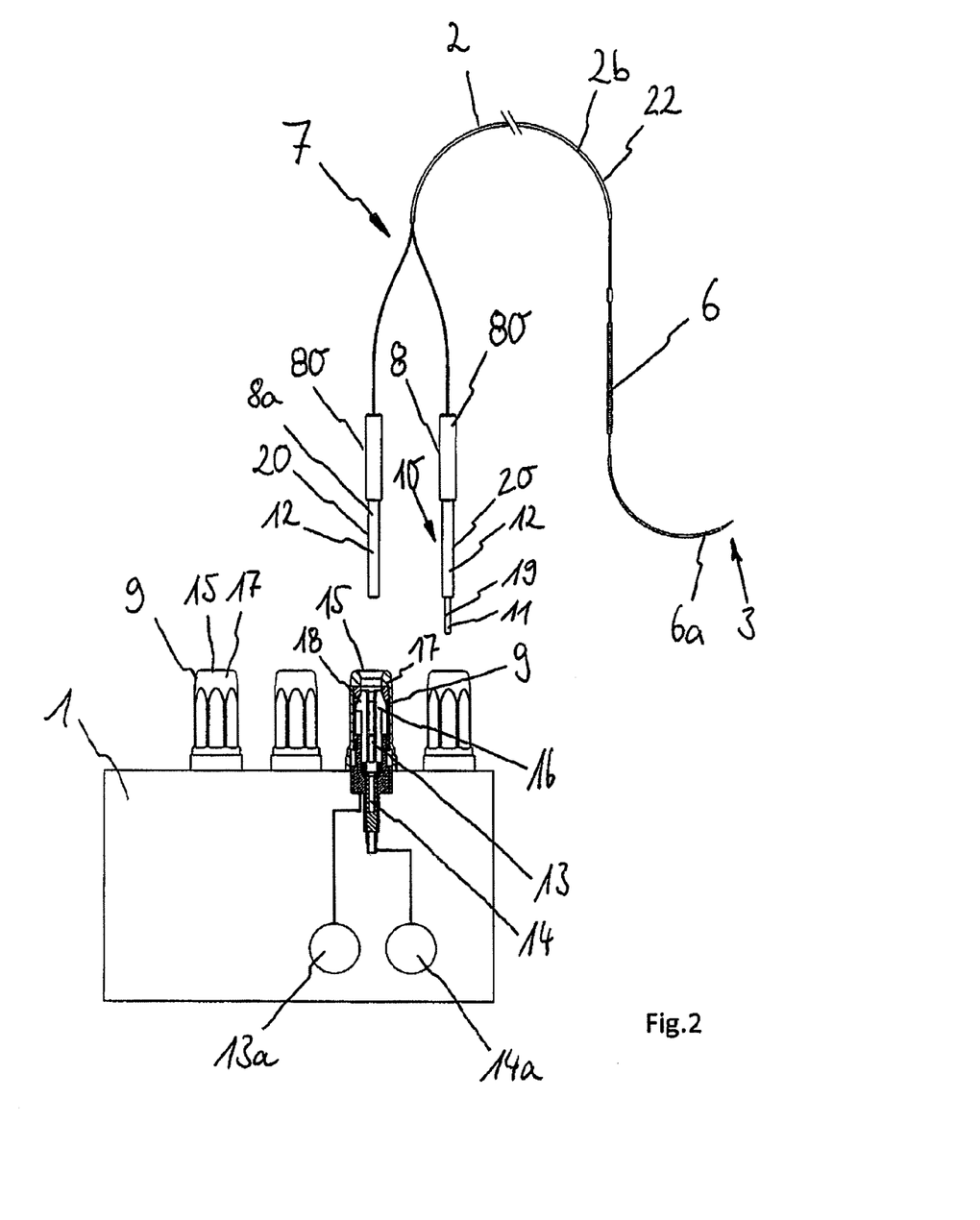
FIG. 2 shows the external pacemaker illustrated in FIG. 1 comprising a bipolar electrode having an active region, which makes contact with tissue of the heart, at its distal end and having two contact plugs at its proximal end, wherein one contact plug has only one contact region and is designed only for transmitting stimulation pulses, and the other contact plug has two contact regions and is therefore also designed for transmitting defibrillation and/or cardioversion pulses to the electrode.

FIG. 2 shows an electrode 2b designed for bipolar stimulation and/or defibrillation and/or for cardioversion by virtue of the fact that it has at least two poles and that the electrode 2b has a respective contact plug 8 or 8a for each pole at its proximal end 7 and the pacemaker 1 has at least one plug socket 9 for each of the two contact plugs 8 and 8a.

In this case, the two poles of said electrode 2b are formed on a single active region, which makes contact with the tissue 4 of the heart 5, at the distal end 3 of the electrode 2b and are not indicated separately in the Figures.

The pacemaker 1 illustrated in the Figures comprises at least four individual plug sockets 9, but can also be equipped with further plug sockets 9.

Figure 11:
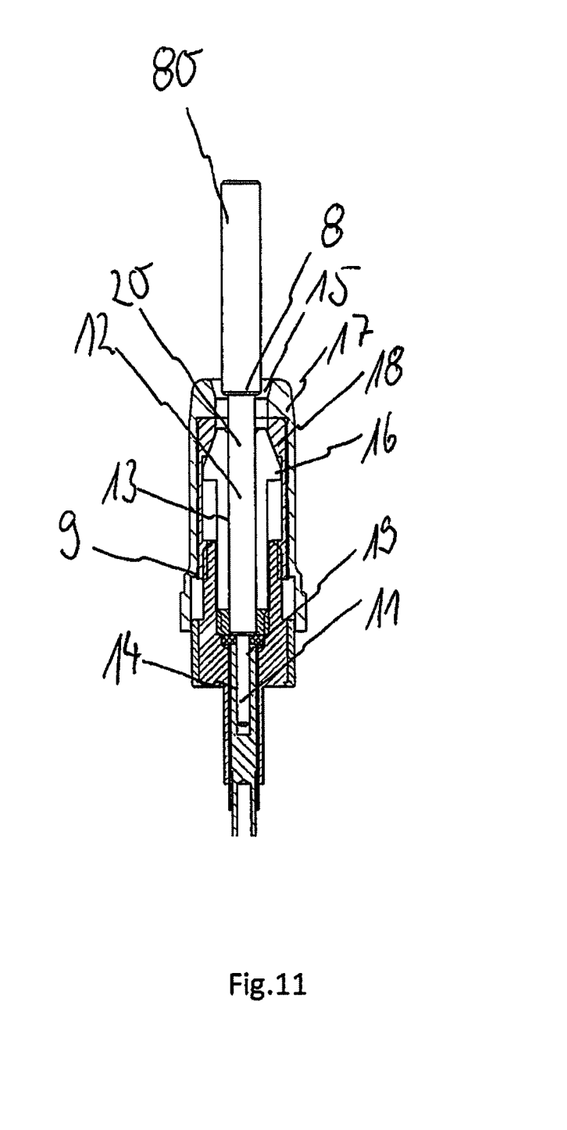
FIG. 11 shows the single-stage contact plug illustrated in FIG. 10 in the plugged-in position of use in the plug socket, wherein the contact plug with its one contact region makes contact only with the first of the two mating contacts.
Figure 12:
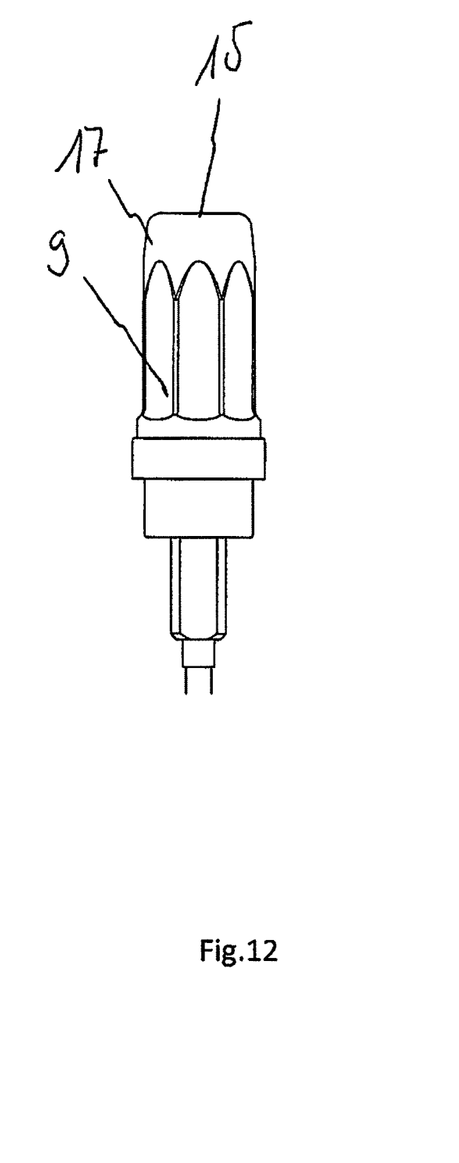
FIG. 12 shows an enlarged side view of the plug sockets illustrated in FIGS. 1 to 5 and 7 to 11.
Figure 13:
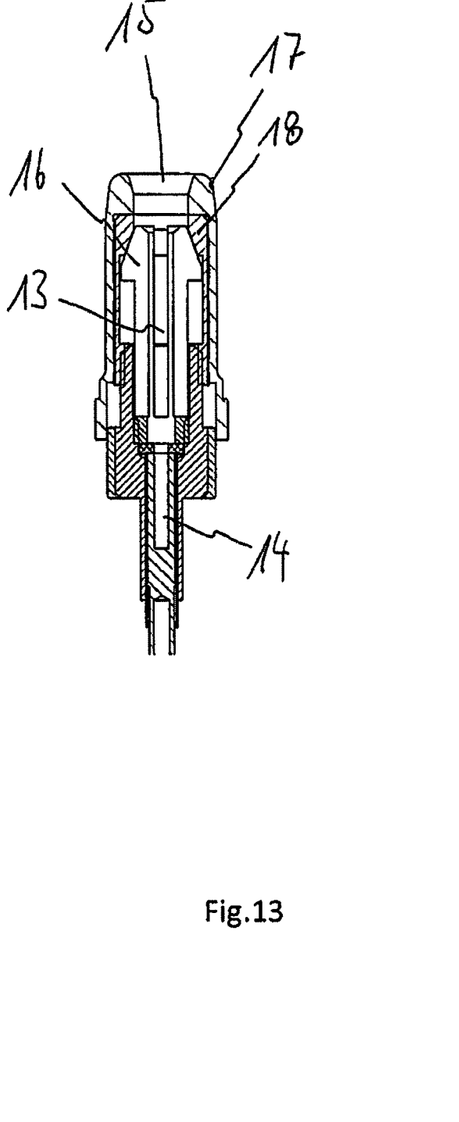
FIG. 13 shows a longitudinal cross-section through the plug socket illustrated in FIG. 12, wherein a collet for a contact plug and the two differently dimensioned and differently configured mating contacts can be discerned.

All of the plug sockets 9 formed at the pacemaker 1 have in their interior the two differently wire-able and differently shaped mating contacts 13 and 14. The construction of the plug sockets 9 can be discerned particularly well with reference to the two FIGS. 11 and 12.

In accordance with FIG. 2, the electrode 2b has two contact plugs 8 and 8a at its proximal end 7. Of these two contact plugs, the contact plug 8 has, as contact regions 11 and 12, the two plug parts 19 and 20 matching the two mating contacts 13 and 14 of the plug socket 9. The contact plug 8 is thus embodied in two stages and, on account of its two differently configured plug parts 19 and 20, is also suitable for transmitting a defibrillation and/or cardioversion pulse to the electrode 2b.

The second contact plug 8a is a conventional contact plug which is embodied in a single stage and the plug part 20 of which makes contact only with the mating contact 13 of the plug socket 9 in the position of use and which serves as an opposite pole for the defibrillation and/or cardioversion, that is to say conducting away the defibrillation and/or cardioversion pulse, but can also be used for transmitting and/or conducting away stimulation pulses.

Figure 3:
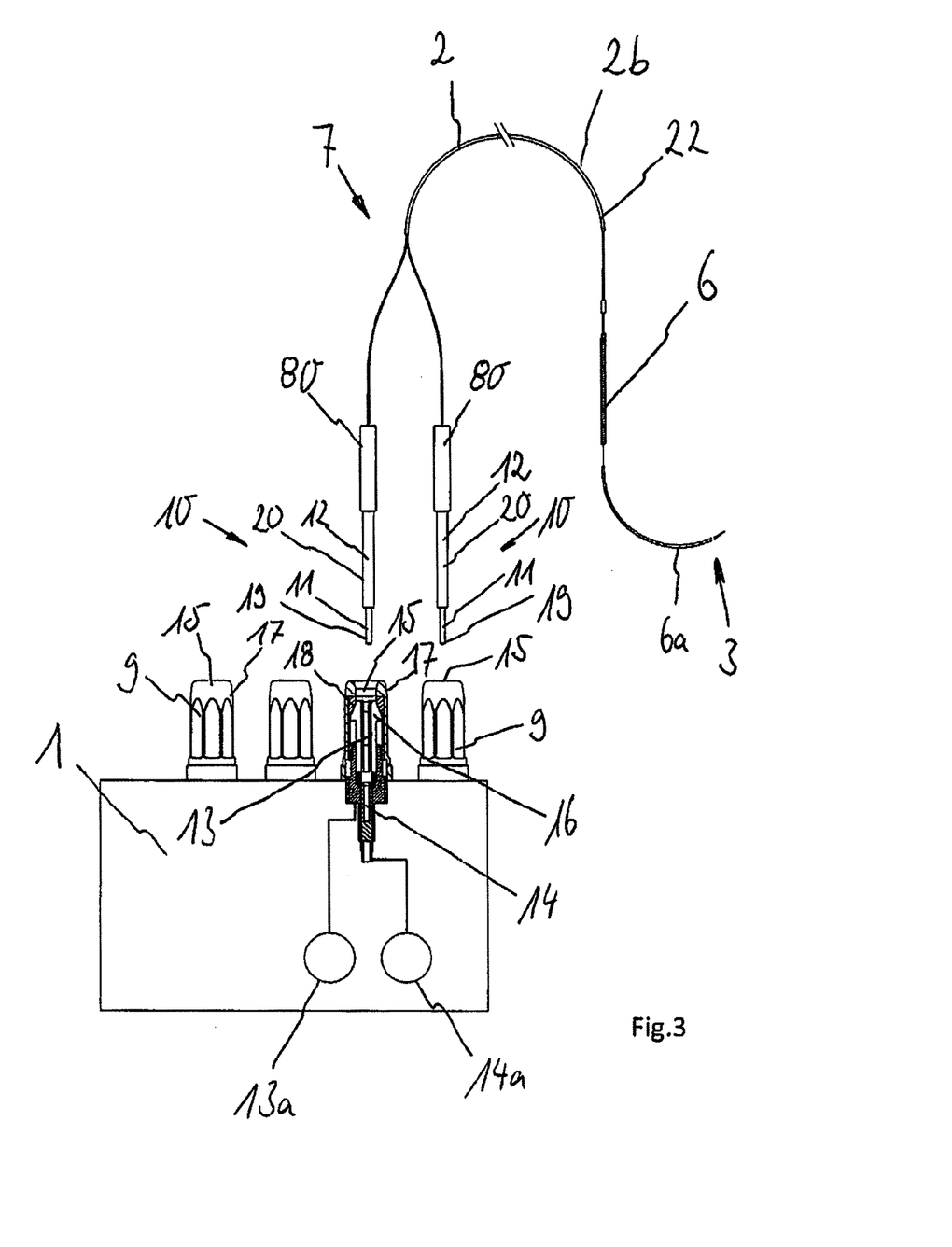
FIG. 3 shows the external pacemaker illustrated in FIGS. 1 and 2 comprising a bipolar electrode having two two-stage contact plugs at its proximal end.

FIG. 3 shows a slightly modified embodiment of the bipolar electrode 2b in comparison with FIG. 2. The electrode 2b here has a respective contact plug 8 for each pole at its proximal end 7.

Both contact plugs 8 are embodied in two stages and each have two differently configured plug parts 19 and 20, which form the contact regions 11 and 12 for the two mating contacts 13 and 14 of the plug socket 9.

In the case of such an electrode 2b, the defibrillation and/or cardioversion pulse can be transmitted to the electrode 2 both via one and via the other of the two contact plugs 8.

Figure 4:
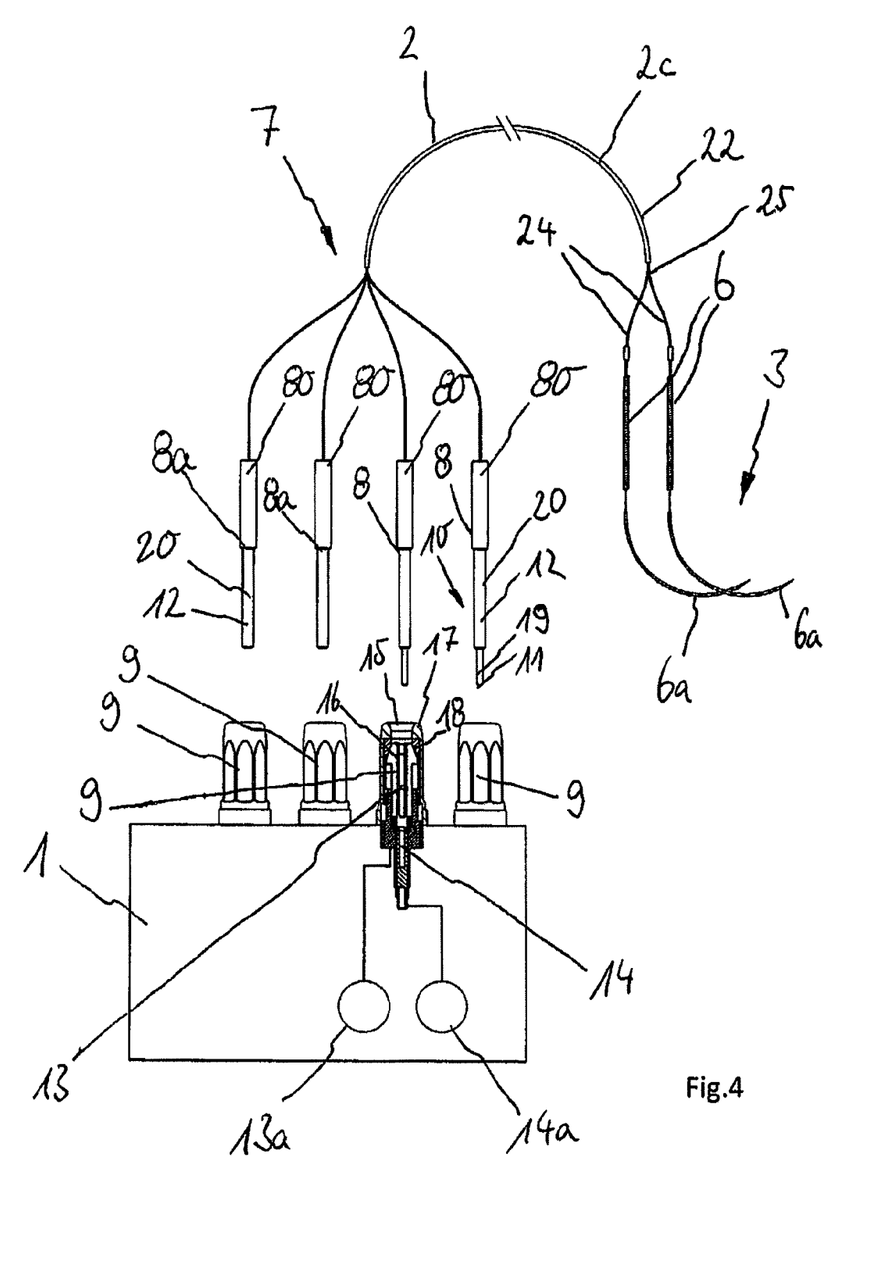
FIG. 4 shows the external pacemaker illustrated in FIGS. 1 to 3 comprising a quadripolar electrode having two implantable regions at its distal end and having four contact plugs at its proximal end, of which two contact plugs respectively have two contact regions and are embodied as multi-stage plugs.
Figure 5:
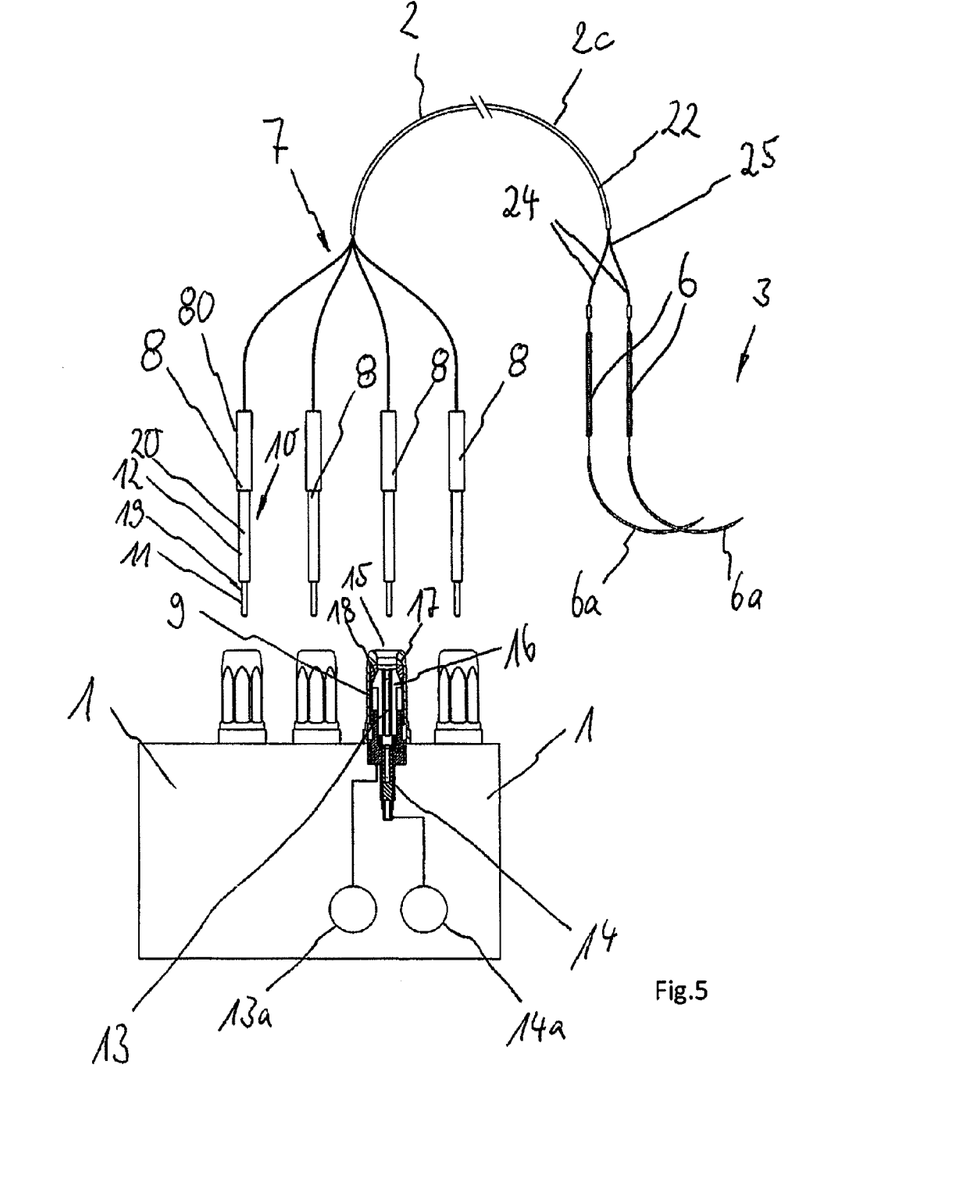
FIG. 5 shows the external pacemaker illustrated in FIGS. 1 to 4 comprising a quadripolar electrode having two implantable regions at its distal end and having four contact plugs at its proximal end, wherein all four contact plugs are embodied in each case in a multi-stage fashion.

FIGS. 4 and 5 show a further embodiment of an electrode according to the invention. The electrode 2c shown is embodied as a quadripolar electrode and has one contact plug for each pole, that is to say a total of four contact plugs 8 and 8a, at its proximal end 7. At its distal end 3, said electrode 2c has two cardiac needles 6a, with the aid of which the regions 6 that are implantable in the tissue of the heart 5 are positioned in the tissue. The two regions 6 are formed adjacent to a branch junction 25 of the electrode 2c in each case at a separate electrode branch 24 and each have two of the total of four poles.

In accordance with FIG. 4, the two contact plugs 8 of the four contact plugs in each case have the two-stage configuration having two different plug parts 19 and 20, while the two remaining contact plugs 8a each have only one plug part 20, which is designed for transmitting the stimulation pulse to the electrode 2 from the first mating contact 13 of the respective plug socket 9.

In the case of the electrode 2c illustrated in FIG. 5, all four contact plugs 8 each have two differently configured plug parts 19 and 20. Thus, all of the contact plugs 8 can be used not only for transmitting a stimulation pulse but also for transmitting a defibrillation and/or cardioversion pulse to the electrode 2c.

In all of the embodiments it should be pointed out that, for transmitting a defibrillation and/or cardioversion pulse to the electrode 2, 2a, 2b, 2c, 2d, at least one pole must be connected to two differently configured plug parts 19 and 20 via a contact plug 8 embodied in two stages, in order to transmit the defibrillation and/or cardioversion pulse from the plug socket 9 to the electrode 2, 2a, 2b, 2c or 2d.

All of the contact plugs 8 shown in the Figures are either connected to the electrode 2, 2a, 2b, 2c or 2d in the delivery state or else subsequently connectable to the electrode 2, 2a, 2b, 2c or 2d or couplable thereto.

In the exemplary embodiments shown in FIGS. 1 to 5, the electrode 2, 2a, 2b and 2c is embodied as a cardiac wire 22, which predominantly after cardiosurgical operations is sewn directly to the heart 5 and is guided through an opening introduced below the sternum toward the outside through the skin, in order to be coupled to the external pacemaker 1.

Figure 14:
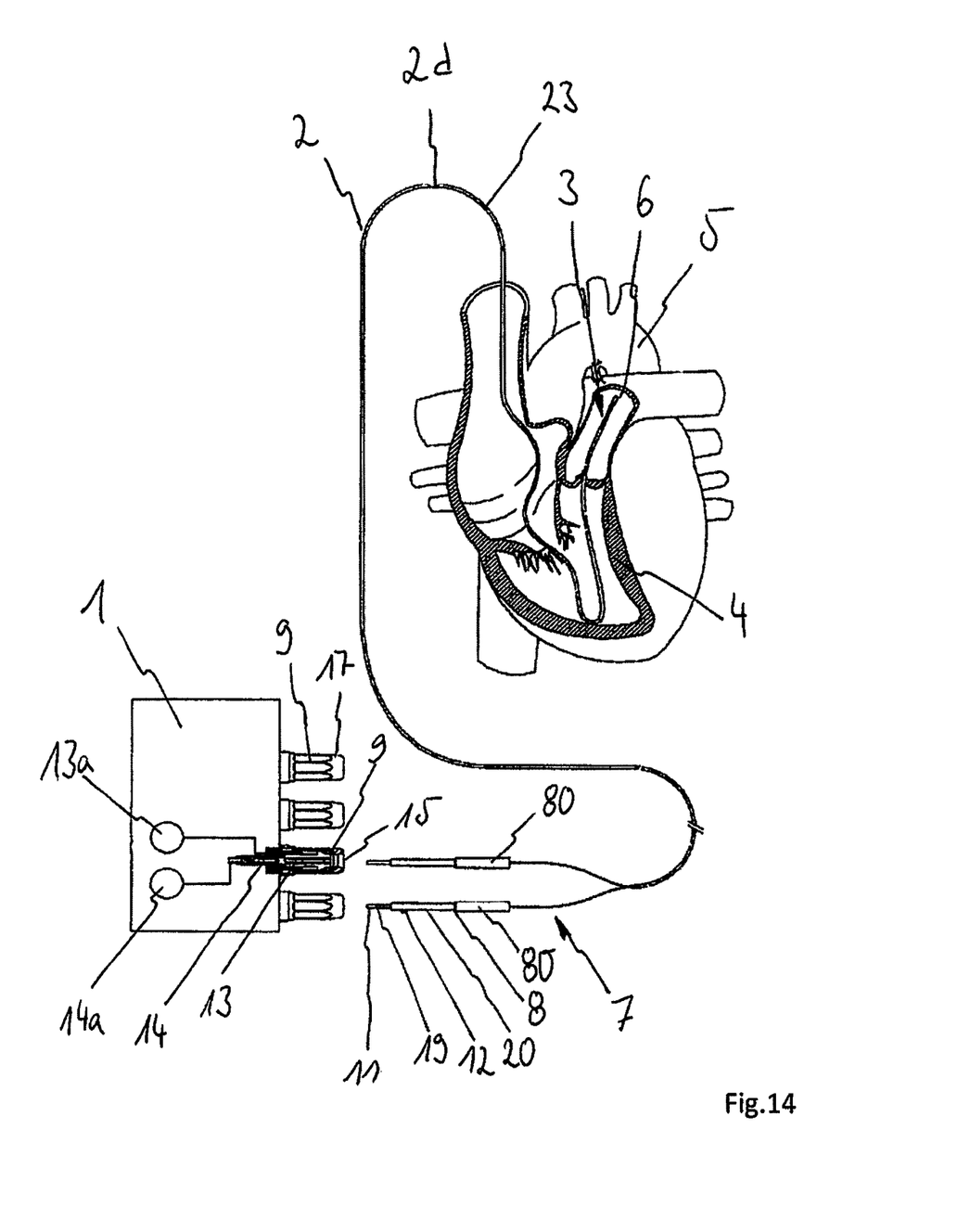
FIG. 14 shows the external pacemaker illustrated in FIGS. 1 to 5 comprising an electrode having two contact plugs at its proximal end, said electrode being embodied as an intracardially feedable catheter and being situated in its use position inserted into a patient's heart.

The electrode 2d shown in FIG. 14 is a bipolar electrode having two contact plugs 8 at its proximal end 7, both of which contact plugs are embodied in two stages and have two plug parts 19 and 20 in each case. This electrode 2d here is designed as an intracardially feedable catheter 23 which is advanced from the outside via a blood vessel into the interior of the heart 5, in order there to emit stimulation and/or defibrillation and/or cardioversion pulses to the patient's heart 5.

In this case, for the emission of stimulation and/or defibrillation and/or cardioversion pulses via the active region 6 to the tissue 4 of the heart 5, there is no need for direct touching contact between the active region 6 and the tissue 4. Due to the electrical conductivity of blood and other body fluids, the pulses can already be transmitted when the active region 6 has only been brought close to the tissue 4 but is not yet directly touching the latter.

The external pacemaker 1 comprises the at least one electrode 2, 2a, 2b, 2c, 2d which can be temporarily connected to the heart 5 and at the distal end 3 of which an active region 6, which makes contact with the tissue 4 of the heart 5, is arranged and at the proximal end 7 of which at least one contact plug 8, 8a is arranged. The electrode 2, 2a, 2b, 2c, 2d is suitable for the transmission of stimulation and/or defibrillation and/or cardioversion pulses and for this purpose can be plugged into the plug socket 9 at the pacemaker 1. In this case, the contact plug 8 has the contact region 11 at its plug part 19 and the contact region 12 at its plug part 20. The plug socket 9 is embodied in a manner matching the contact plug 8 and has the two mating contacts 13 and 14, of which the first mating contact 13 is designed for transmitting stimulation pulses and the second mating contact 14 is designed for transmitting defibrillation and/or cardioversion pulses to the contact plug 8. In the plugged-in position of use, only the contact region 11 at the plug part 19 makes contact with the mating contact 14 provided for transmitting the defibrillation and/or cardioversion pulses, with the result that no defibrillation and/or cardioversion pulse can be transmitted to electrodes which are unsuitable for defibrillation and/or cardioversion and have only a single-stage contact plug 8a.

The invention claimed is:

1. An external pacemaker (1) comprising at least one electrode (2, 2a, 2b, 2c, 2d) which is temporarily connectable to a heart and at a distal end (3) of which is arranged at least one active region (6) which makes contact with tissue (4) of the heart (5) of a patient in a position of use, the electrode (2, 2a, 2b, 2c, 2d), in the position of use, is joinable or joined to the external pacemaker (1) by a proximal end (7) of said electrode via at least one plug connector, including a contact pin (8, 8a) and a plug socket (9), for transmitting stimulation pulses from the external pacemaker (1) to the heart (5) of the patient, and the electrode (2, 2a, 2b, 2c, 2d), at least at an active region (6) thereof which makes contact with the tissue of the heart (5), has a surface area large enough for transmission or emission of a defibrillation and/or cardioversion pulse, and the contact pin (8) of the plug connector has a first and a second electrical contact portion (11, 12) and the plug socket (9) of the plug connector, in a manner matching the contact pin, has a first and a second electrical mating contact (13, 14), and the two contact portions (11, 12) or the two mating contacts (13, 14) of that part of the plug connector which is arranged at the external pacemaker (1) are wire-able or wired differently, such that one of the two contact portions (11, 12) or mating contacts (13, 14) is provided for transmitting stimulation pulses and the other of the two contact portions (11, 12) or mating contacts (13, 14) are provided for transmitting at least one of defibrillation or cardioversion pulses to the electrode (2, 2a, 2b, 2c, 2d), and wherein the external pacemaker (1) is at least one of connected to a defibrillator and/or cardioverter, contains a defibrillator and/or a cardioverter, or is designed for emitting defibrillation and/or cardioversion pulses.

2. The pacemaker as claimed in claim 1, wherein the contact plug (8) of the plug connector is arranged at the proximal end (7) of the electrode (2, 2a, 2b, 2c, 2d) and the plug socket (9) of the plug connector is arranged at the external pacemaker (1).

3. The pacemaker as claimed in claim 1, wherein the two differently wire-able or wired mating contacts (13, 14) of the plug socket (9) are have different shapes and the two contact regions (11, 12) of the contact plug (8) are shaped in a manner matching the mating contacts (13, 14), or the two contact regions (11, 12) of the contact plug (8) are embodied as two plug parts (19, 20) matching the two mating contacts (13, 14) of the plug socket (9).

4. The pacemaker as claimed in claim 1, wherein the first and second mating contacts (13, 14) of the plug socket (9) are arranged one behind the other in a plug-in direction of the contact plug (8, 8a) and have two internal cross sections of different sizes.

5. The pacemaker as claimed in claim 4, wherein the first mating contact (13) of the plug socket (9) has a larger internal cross section than the second mating contact (14) and is embodied as a contact area for transmitting stimulation pulses to the electrode (2, 2a, 2b, 2c, 2d), and the second mating contact (14) of the plug socket (9), which is adjacent in the plug-in direction of the contact plug (8, 8a), has a smaller internal cross section than the first mating contact (13), and is embodied as a contact area for transmitting at least one of defibrillation or cardioversion pulses to the electrode (2, 2a, 2b, 2c, 2d).

6. The pacemaker (1) as claimed in claim 5, wherein the first mating contact (13) having the larger internal cross section, in the position of use, is arranged in a manner adjoining an entrance opening (15) of the plug socket (9) for the contact plug (8, 8a), and the second mating contact (14) having the smaller internal cross section follows therebehind in the plug-in direction of the contact plug (8, 8a).

7. The pacemaker (1) as claimed in claim 1, wherein the plug socket (9) has in the first mating contact (13) at least one of a collet form or a slotted region having individual fingers which are compressible by a union nut (17) and a conical region (18), or has contact springs in the second mating contact (14).

8. The pacemaker as claimed in claim 1, wherein first and second plug parts (19, 20) form the contact regions (11, 12) of the contact plug (8) and matching the two mating contacts (13, 14) of the plug socket (9), the first and second plug parts are arranged one behind the other in the plug-in direction of the contact plug (8, 8a) and are embodied with different cross sections such that the second plug part (20) of the contact plug (8), which makes contact with the first mating contact (13) of the plug socket (9) in the plugged-in position of use, at least in regions projects radially beyond the first plug part (19) of the contact plug (8), the first plug part is arranged behind said second plug part in an axial direction and makes contact with the second mating contact (14) of the plug socket (9) in the plugged-in position of use.

9. The pacemaker as claimed in claim 8, wherein the first and second plug parts (19, 20) of the contact plug (8) each have at least one of a closed or circular cross section.

10. The pacemaker as claimed in claim 9, wherein the first plug part (19) of the contact plug (8) has a polygonal cross section, and the second plug part (20) of the contact plug (8) has a round cross section.

11. The pacemaker as claimed in claim 8, wherein the second plug part (20) of the contact plug (8) having the larger cross section has a circular cross section, and the first plug part (19) of the contact plug (8) having the smaller cross section has an arbitrary cross-sectional shape, a largest dimension of the first, smaller plug part (19) is enclosed by a projection of the circular cross section of the second, larger plug part (20) of the contact plug (8).

12. The pacemaker as claimed in claim 8, wherein longitudinal central axes of the two plug parts (19, 20) of the contact plug (8) are arranged at least one of coaxially with respect to one another, in alignment with one another, or extending parallel and offset with respect to one another.

13. The pacemaker as claimed in claim 8, wherein at least one of the two plug parts (19, 20) of the contact plug (8) has a cross section which deviates from a circular form and is one of oval, triangular, quadrilateral, polygonal, or circular with at least one flattened portion.

14. The pacemaker as claimed in claim 1, wherein the electrode (2, 2a, 2b, 2c, 2d) is for at least one of bipolar, quadripolar, or multipolar stimulation, or defibrillation or cardioversion and includes two or more poles, and a respective one of the plug connectors, including one of the contact plugs (8, 8a) and a respective one of the plug sockets (9), is provided for each of the poles of the electrode (2, 2a, 2b, 2c, 2d).

15. The pacemaker as claimed in claim 1, wherein the electrode (2, 2a, 2b, 2c, 2d) has at a distal end (3) thereof at least one second active region (6) which makes contact with the tissue (4) of the heart (5) of a patient.

16. The pacemaker as claimed in claim 1, wherein the contact plug (8, 8a) is at least one of connected to, connectable to, or coupleable to the electrode (2, 2a, 2b, 2c, 2d).

17. The pacemaker as claimed in claim 1, wherein the electrode (2) is embodied as a cardiac wire (22) or as an intracardially feedable catheter (23).

18. The pacemaker as claimed in claim 1, wherein a cross-sectionally thinner first part of the contact plug (8) that fits into the second mating contact (14) of the plug socket (9), is at least on of slotted or elastically deformable, and the contact plug (8), in the position of use, is at least one of held or fixedly clamped in a force-locking manner in the plug socket (9) by at least one of the contact regions (11, 12) of said contact plug.

19. The pacemaker as claimed in claim 1, wherein at least one pole is arranged at each of the active regions (6).

* * * * *